United States Patent [19]
Wenstrom, Jr. et al.

[11] Patent Number: 6,045,573
[45] Date of Patent: Apr. 4, 2000

[54] SUTURE ANCHOR HAVING MULTIPLE SUTURES

[75] Inventors: Richard F. Wenstrom, Jr., Norwood; Ronald L. Taylor, Jr., Everett, both of Mass.; Steven L. Jensen, Brigham City, Utah

[73] Assignee: Ethicon, Inc., Somerville, N.J.

[21] Appl. No.: 09/235,367

[22] Filed: Jan. 21, 1999

[51] Int. Cl.[7] ................................................. A61B 17/04
[52] U.S. Cl. .............................................. 606/232; 606/73
[58] Field of Search ............................... 606/73, 232, 60, 606/72, 75, 104

[56] References Cited

U.S. PATENT DOCUMENTS

| | | |
|---|---|---|
| 3,579,831 | 5/1971 | Stevens ........................................ 606/73 |
| 4,898,156 | 2/1990 | Gatturna et al. . |
| 5,013,316 | 5/1991 | Goble et al. . |
| 5,152,790 | 10/1992 | Rosenberg et al. . |
| 5,207,679 | 5/1993 | Li . |
| 5,217,486 | 6/1993 | Rice et al. . |
| 5,411,506 | 5/1995 | Goble et al. . |
| 5,411,523 | 5/1995 | Goble . |
| 5,417,712 | 5/1995 | Whittaker et al. . |
| 5,443,482 | 8/1995 | Stone et al. . |
| 5,505,735 | 4/1996 | Li . |
| 5,522,845 | 6/1996 | Wenstrom, Jr. . |
| 5,584,835 | 12/1996 | Greenfield . |
| 5,683,418 | 11/1997 | Luscombe et al. . |
| 5,814,070 | 9/1998 | Borzone et al. . |
| 5,824,011 | 10/1998 | Stone et al. . |

*Primary Examiner*—Michael Buiz
*Assistant Examiner*—Julian W. Woo
*Attorney, Agent, or Firm*—Emil Richard Skula

[57] ABSTRACT

A suture anchor for attaching soft tissue to bone. The anchor has a body member and a longitudinal axis. The anchor contains at least two suture mounting passages for mounting suture to the anchor. A first passage is located proximally to the second passage.

20 Claims, 10 Drawing Sheets

SUTURE ANCHOR HAVING MULTIPLE SUTURES

TECHNICAL FIELD

The field of art to which this invention pertains is soft tissue fixation devices, in particular, suture anchors.

BACKGROUND OF THE INVENTION

Medical devices useful for fixating soft tissue are known in the art. These devices include screws, bone pins, staples, sutures and suture anchors. Of particular interest in orthopedic reconstructive surgery are suture anchors. Suture anchors typically consist of a member having a suture mounted thereto. Surgical needles are usually mounted to the ends of the suture. A suture anchor is typically inserted into a bore hole drilled into a bone. The suture extends out from the bore hole and is used to attach soft tissue such as joint cartilage to the surface of the bone.

Several types of suture anchor devices are known in the art. One type of suture anchor is known as a "arced" anchor. This type of suture anchor is disclosed in U.S. Pat. Nos. 4,898,156, 5,207,679, 5,217,486, 5,417,712, 5,505,735, and 5,522,845 which are incorporated by reference. The arced anchor may have a cylindrical body member. Deformable arc members extend from the body member. Suture is typically mounted in a suture mounting hole in the anchor member or about the anchor member for example in an eyelet. The arc members are deformed backward during insertion by the hard outer cortex of the bone as the anchor is inserted into a bone bore hole. When in place in the bone bore hole, the arcs subsequently relax in the cancellous bone region, allowing the arcs to engage cancellous bone and thereby fixating the suture anchor in the bore hole. Another type of suture anchor is a threaded anchor. Many threaded anchors are self-tapping and do not require a pre-drilled bone bore hole, while other anchors require a drilled and tapped bore hole. The anchors have an elongated body with a distal point end and a plurality of thread flights. The threaded anchors may have an optional cutting flute. The threaded anchors typically have a proximal drive end that is engaged by a driving instrument to rotate the threaded anchor into position within the bone. A suture is typically mounted to the anchor, for example, in a hole contained in the anchor body or to an eyelet. Examples of screw threaded suture anchors are contained in U.S. Pat. Nos. 5,013,316, 5,411,506 and 5,411,523 which are incorporated by reference.

Another type of suture anchor that is known in this art is referred to as a "wedge" suture anchor. The wedge anchor typically has a triangular profile. A suture is typically mounted in a hole contained in the wedge anchor body. The wedge anchor is inserted into a bone bore hole and caused to partially rotate, thereby causing one or more edges to engage bone. Examples of wedge anchors are contained in U.S. Pat. No. 5,683,418, which is incorporated by reference. Other types of suture anchors are also known in the art including force-fit anchors having compressible anchor bodies, two-piece umbrella-type anchors that are expanded after placement in a bone bore hole, and temperature induced shape-memory anchors.

Most suture anchors utilize some type of a mounting hole in the anchor body to mount a suture. The mounting hole is typically transverse to the longitudinal axis of the anchor body. Typically the mounting hole is contained in the proximal section of the anchor, although it can be at the middle, or in a distal section.

Most suture anchors have a single strand of suture mounted to the anchor. For most soft tissue fixation surgical procedures, this is adequate to achieve the desired amount of soft tissue fixation to the bone surface. However, certain procedures require the use of more than one suture to obtain satisfactory soft tissue fixation. For example, multiple sutures are often needed in surgical procedures to repair the rotator cuff, in plastic surgery, in cosmetic procedures, and in surgical procedures involving repair of the knee, ankle, elbow, hand Achilles tendon, etc.

Presently, when more than one suture is necessary, typically, suture anchors are used having two or more strands of suture mounted in a single suture mounting hole. The opening in the anchor can be enlarged to accommodate multiple suture stands. However, there are problems associated with the use of such suture anchors in surgical procedures. The problems include suture binding, tangling, inadvertent knotting and twisting, all of which may interfere with the surgeon's ability to efficiently perform a surgical procedure.

Accordingly there is a need in this art for novel suture anchors that can be used with multiple suture anchors, which overcome these problems.

DISCLOSURE OF THE INVENTION

Therefore, it is an object of the present invention to provide novel suture anchors that can have multiple sutures mounted thereto.

It is a further object of the present invention to provide a suture anchor having at least two suture mounting passages that are angulated with respect to each other.

Accordingly, a novel suture anchor is disclosed. The suture anchor has a body member having a distal end, a proximal end, and outer surface and a longitudinal axis. A first suture passage extends through the body member, said first passage is substantially transverse to the longitudinal axis. A second suture passage extends through the body member, said second passage is located proximal to the first suture passage, said second suture passage is substantially transverse to the longitudinal axis. The second suture passage is angulated with respect to the first suture passage.

Another aspect of the present invention is a method of using the afore-described suture anchor in a surgical procedure.

The foregoing and other features and advantages of the present invention will become more apparent from the following description and accompanying drawings.

DESCRIPTION OF THE PREFERRED EMBODIMENTS

The suture anchors of the present invention may be constructed from conventional implantable bio-compatible materials. The materials may be non-absorbable materials such as stainless steel, nickel-titanium alloy, titanium, gold, ceramic, and the like and equivalents thereof. The sutures may also be manufactured from conventional absorbable bio-compatible polymeric materials including polylactones, polylactides, polyesters, polygalactides, polydioxanone, polycaprolactone, copolymers and blends thereof, hydroxy apetite, ceramics, and the like and equivalents thereof.

The sutures which are mounted to the suture anchors of the present invention are formed from conventional polymeric materials and may be absorbable or non-absorbable. Examples of non-absorbable materials include silk, polyethylene, polypropylene, polyvinylidene fluoride, polyesters and the like. Examples of absorbable suture materials include cat gut (collagen), aliphatic polyesters, lactide, glycolide, trimethylene carbonate, polycaprolactone, polydioxanone, and copolymers and blends thereof and the like.

Figure 1:
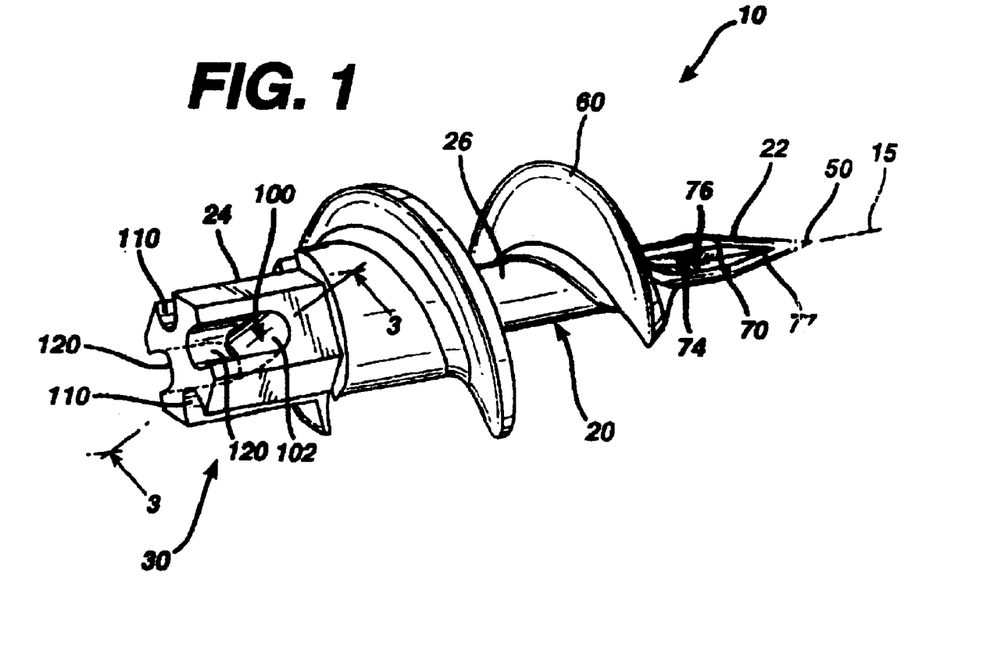
FIG. 1 is a perspective view of a preferred embodiment of a suture anchor of the present invention.
Figure 2:
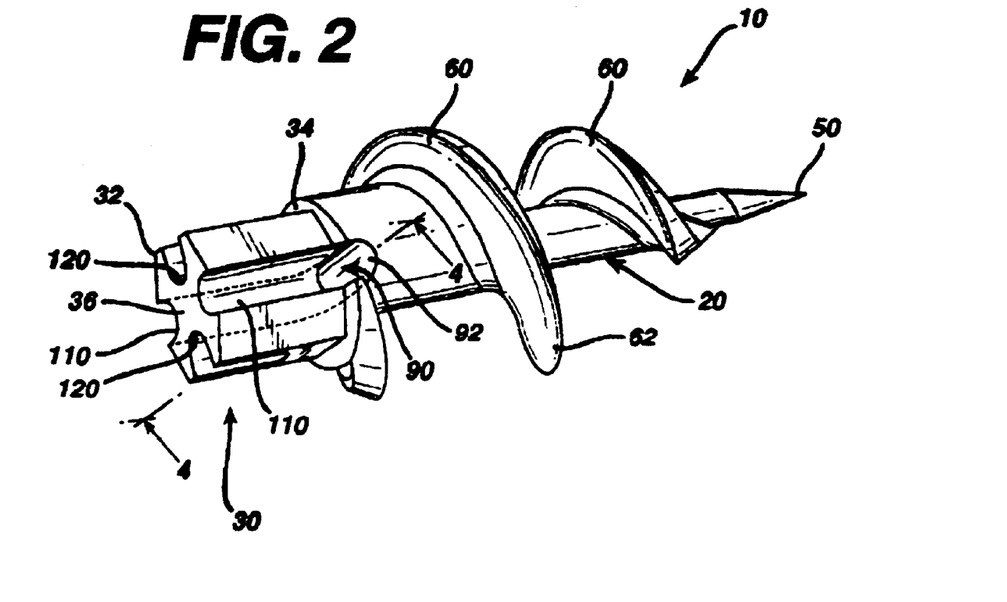
FIG. 2 is a perspective view of the opposite side of the suture anchor of FIG. 1.
Figure 3:
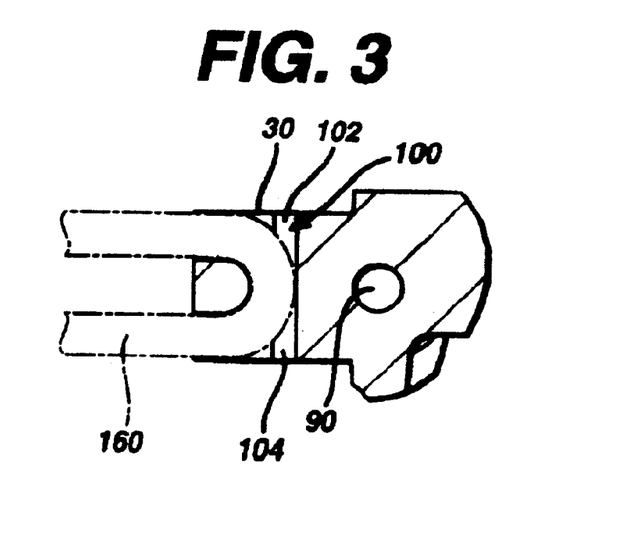
FIG. 3 is a partial cross-sectional view of the proximal end of the suture anchor of FIG. 1 taken along view line 3—3.
Figure 4:
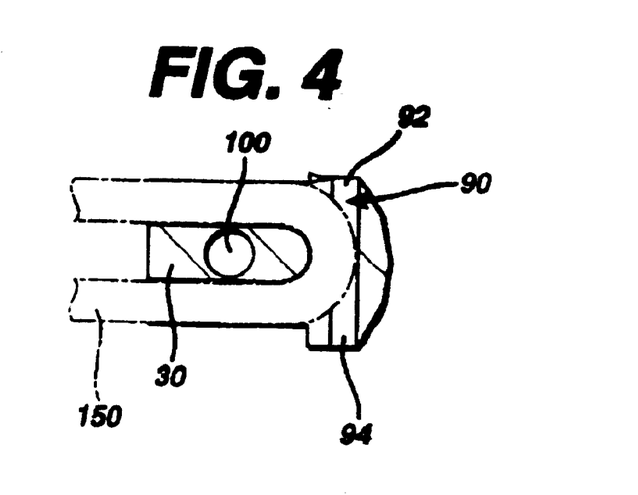
FIG. 4 is a partial cross-sectional view of the proximal end of the suture anchor of FIG. 2 taken along view line 4—4.
Figure 5:
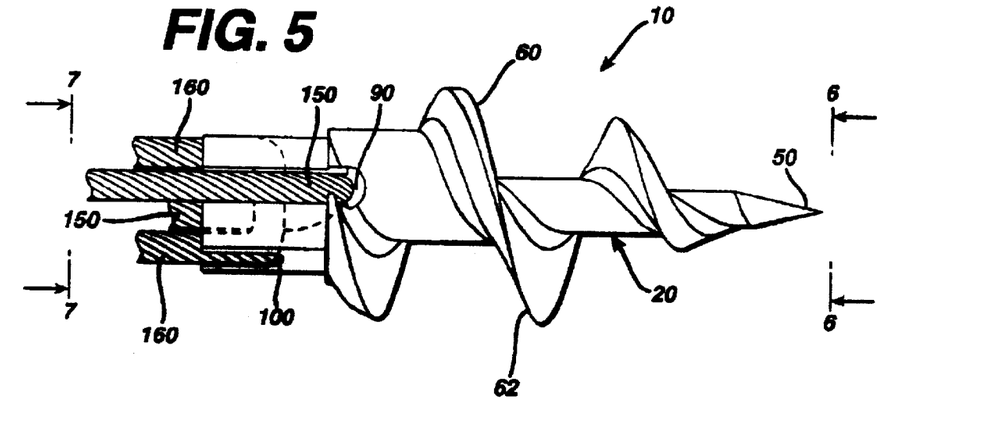
FIG. 5 is a side view of the suture anchor of FIG. 2 illustrating sutures mounted in both mounting passages.
Figure 6:
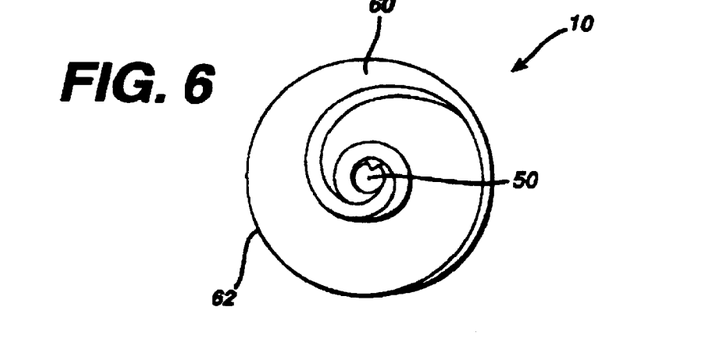
FIG. 6 is an end view taken from view line 6—6 of the suture anchor of FIG. 5.
Figure 7:
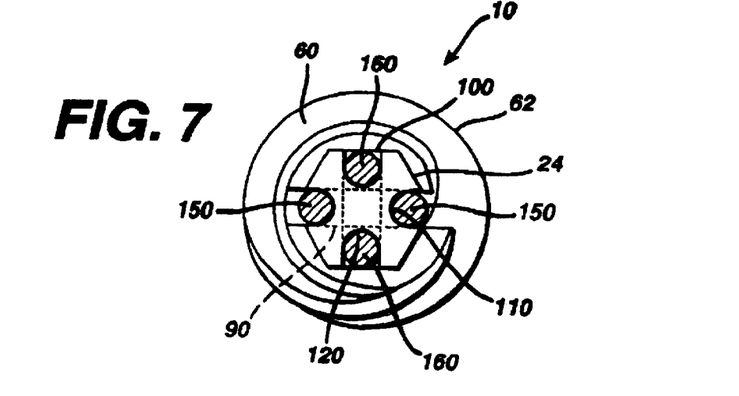
FIG. 7 is an end view of the proximal end of the suture anchor of FIG. 5 taken along view line 7—7.

Referring now to FIGS. 1 and 2, a preferred embodiment of a screw threaded suture anchor of the present invention is illustrated. Anchor 10 is seen to have elongated body member 20. Body member 20 is seen to have distal end 22 and proximal end 24. Extending from the proximal end 24 of body member 20, is the driving end 30. Driving end 30 is seen to have distal end 34 and proximal end 32. As seen in FIG. 7, the driving end 30 is seen to have top flat surface 36. In addition, the driving end 30 is seen to have a substantially hexagonal cross-section as seen in FIG. 7. Although a hexagonal cross-section is preferred, the driving end 30 may have any desired geometric cross-section including triangular, rectangular, square, poligimal, and the like. The anchor 10 is also seen to have longitudinal axis 15. The body member 20 is seen to have outer surface 26. Extending distally from the proximal end 22 of body member 20, is the distal point 50. The anchor 10 is also seen to have a plurality of helical screw thread flights 60 extending outwardly from the surface 26. The flights 60 are seen to have outer edges 62. Contained in the proximal end 22 of member 20, is the cutting flute 70 having cutting edges 74 and bottom 76. The distal end 77 of the flute 70 is seen to extend into the distal point 50. Contained in the proximal end 24 of the body member 20 is the first transverse suture mounting passage 90. Passage 90 is seen to extend through the proximal end of body member 20 and to have opposed openings 92 and 94. Passage 90 is preferably substantially perpendicular to the longitudinal axis 15, although it may be angulated. Intersecting the ends of the passage 90 are the suture containment slots 110 which extend from the surface 36 of the driving end 30 and intersect the passage 90. Located proximal to the first suture mounting passage 90 is the second transverse suture mounting passage 100. Second suture mounting passage 100 is seen to have opposed openings 102 and 104. Passage 100 is also preferably substantially perpendicular to longitudinal axis 15, but may also be angulated if desired. Similarly, suture slots 120 are seen to intersect the passage 100 adjacent to the ends of the passage. As illustrated, it can be seen that the passage 100 is rotated approximately 90° from the passage 90. It is preferred that the passage 100 be angulated with respect to passage 90 and that the angle of rotation be about 90 degrees; although not preferred, passages 90 and 100 may be substantially parallel. Referring now to FIGS. 5 and 7, suture 150 is seen to be mounted in passage 90 and suture 160 is seen to be mounted in passage 100.

Figure 8:
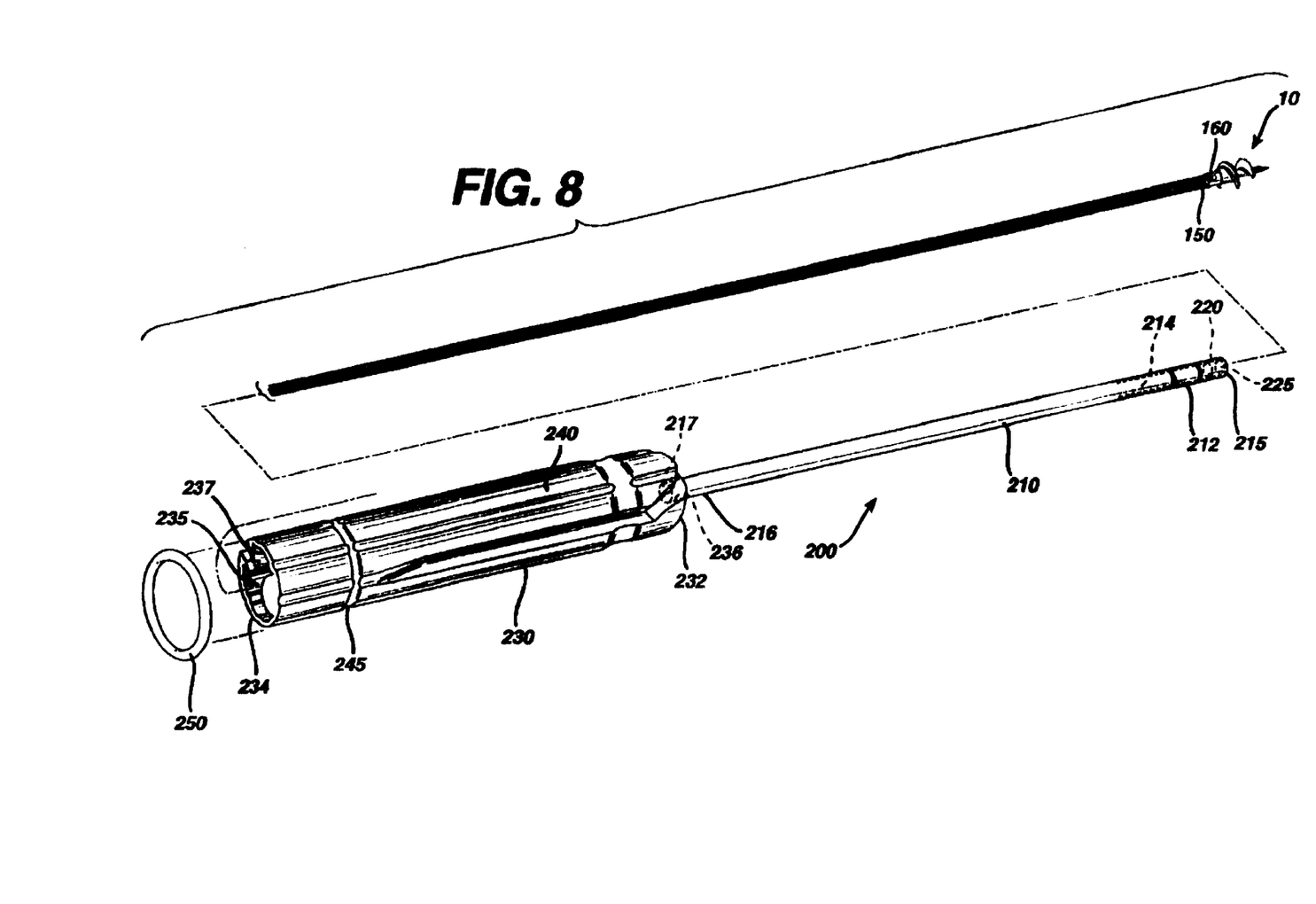
FIG. 8 is an exploded perspective view of the suture anchor of FIG. 5 and a driving instrument.
Figure 9:
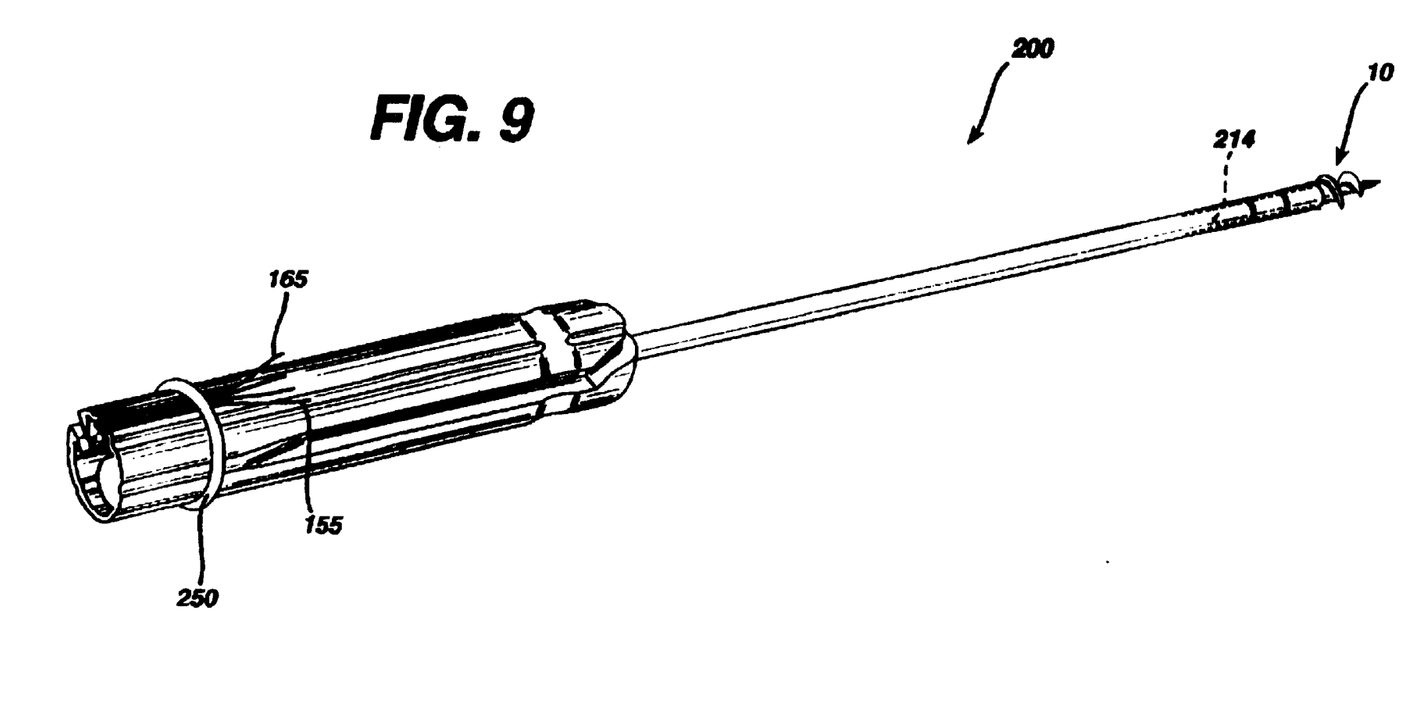
FIG. 9 is a perspective view of a suture anchor of the present invention mounted in a driver instrument.

A driving tool useful for inserting the suture anchor 10 of the present invention into bone is illustrated in FIGS. 8 and 9. As seen in FIGS. 8 and 9, the tool 200 is seen to have distal tubular member 210 and proximal handle 230. Tubular member 210 is seen to have distal end 212 and proximal end 216. Tubular member 210 is also seen to have longitudinal passage 214, distal end opening 215 and proximal end opening 217. Mounted in the distal end 212 of the tubular member 210 is the engagement member 220. Engagement member 220 is seen to contain a socket 225 having a plurality of sides to mate with the driving end 30 of anchor 10. The handle 230 is seen to have distal end 232, proximal end 234, passage 235, distal opening 236 and proximal opening 237. The handle 230 is seen to have exterior ribs 240, and annular groove 245 located toward proximal end 234. The proximal end 216 of tubular member 210 is mounted into distal opening 236 of handle 230 such that the passage 214 of tubular member 210 is in communication with the passage 235 of handle 230.

As seen in FIG. 9, the suture anchor 10 is mounted to the driver tool 200 by inserting the sutures 150 and 160 through the longitudinal passages 214 and 235. Then the driving end 30 of anchor 10 is mounted in the socket 225 of engagement member 220. Then the ends 155 and 165 of the sutures 150 and 160, respectively, are folded back onto the surface of handle member 230 and the elastic retention ring 250 is rolled over the sutures and contained within the annular groove 245, thereby maintaining the sutures in place.

Figure 10:
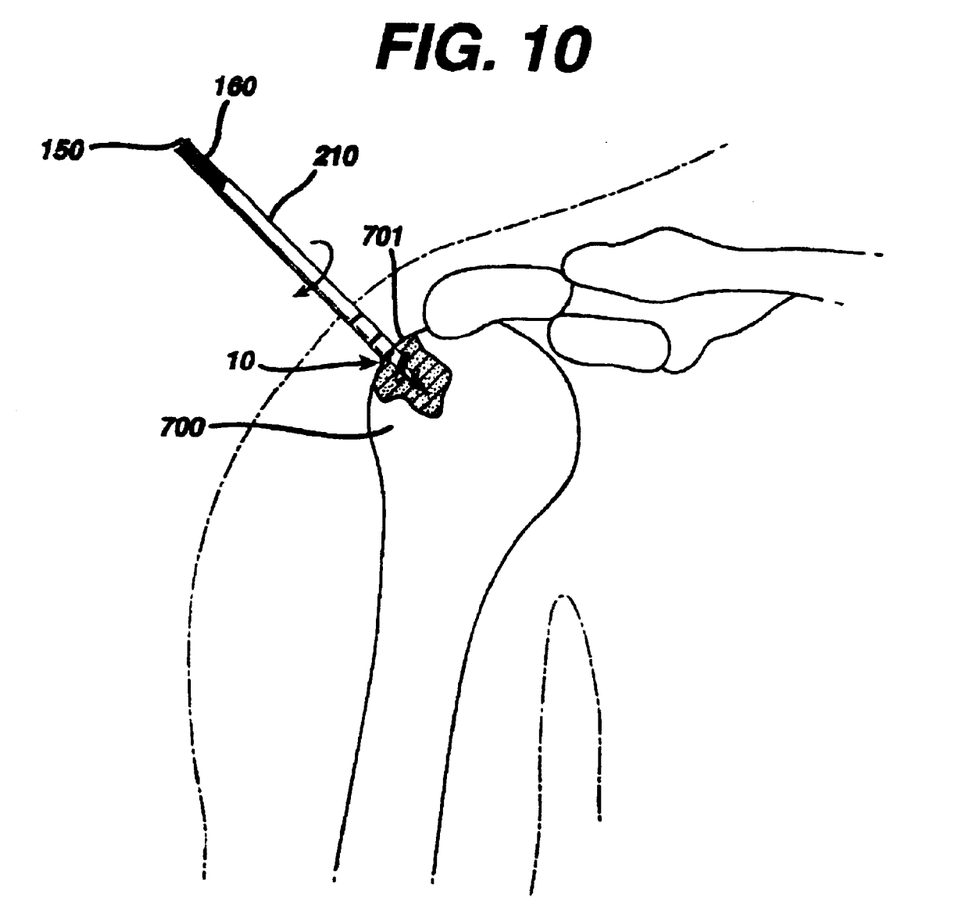
FIG. 10 is a diagram illustrating the insertion of the suture anchor of the present invention into a shoulder bone.
Figure 11:
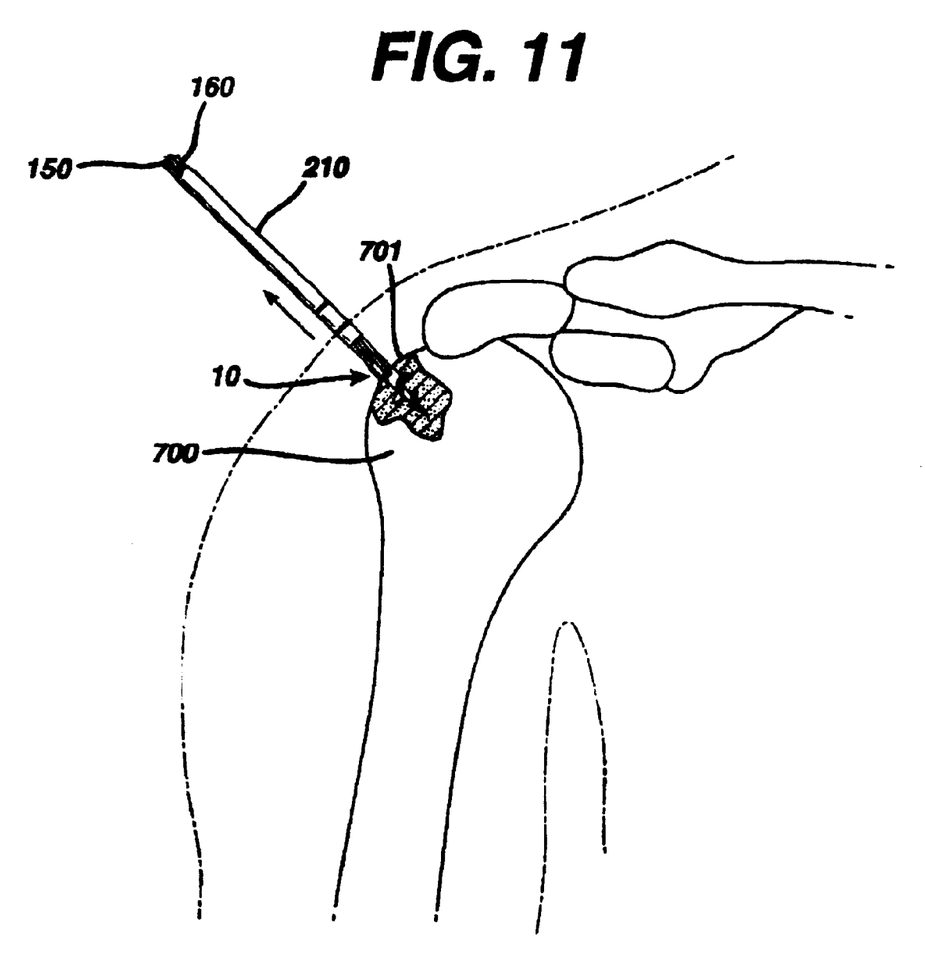
FIG. 11 illustrates the removal of the driver from the suture anchor after the anchor has been implaced in bone.
Figure 12:
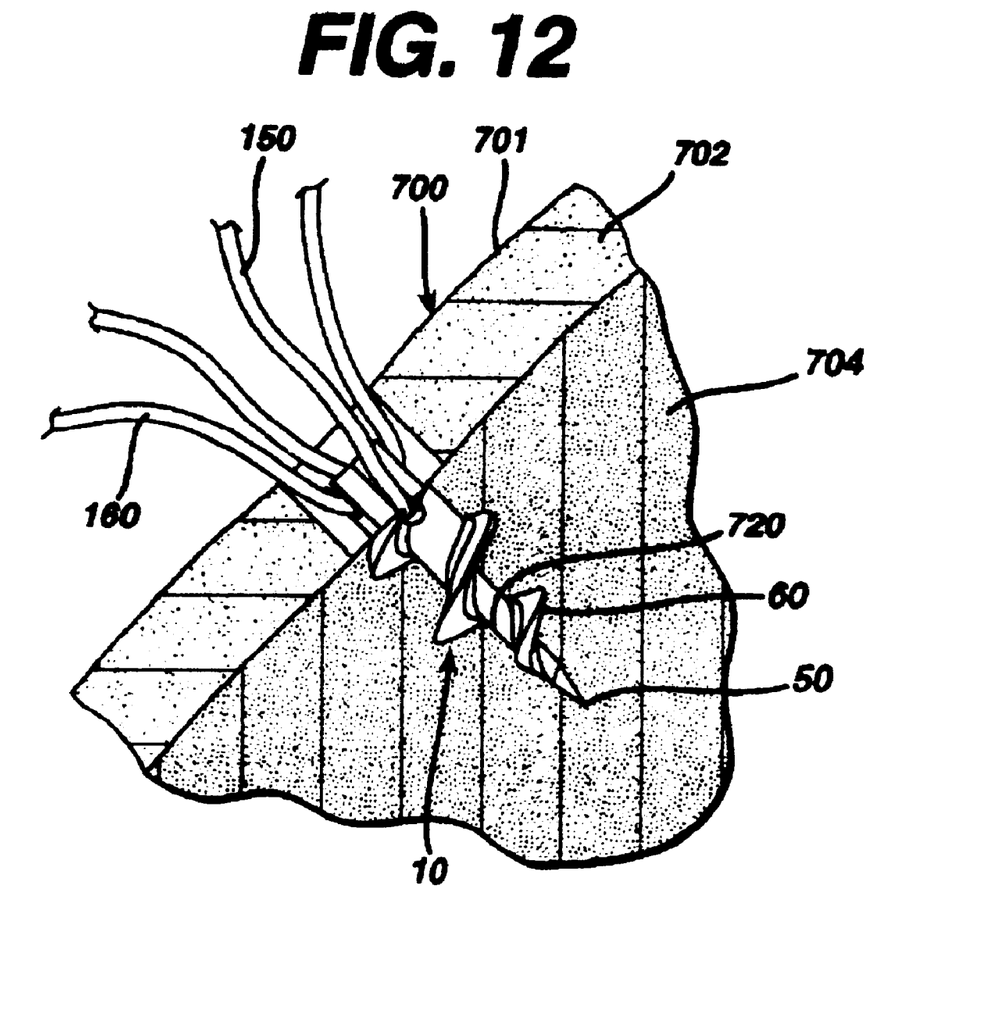
FIG. 12 illustrates a suture anchor of the present invention implaced in bone.

The anchor members 10 of the present invention are typically used in arthroscopic surgical procedures to repair a rotator cuff, but may also be used in open surgical procedures. The anchors are installed as illustrated in FIGS. 10–12. Although not shown, the joint is insufflated with a saline solution. An arthroscope is inserted into the joint. Then, an incision is made to insert the anchor 10 and distal end 212 of the tube 210 into the joint. The surgeon locates the surface 701 of the bone 700 and pushes the distal point 50 of the anchor 10 into the cortex 702 of the bone 700 as he begins to rotate the anchor member by rotating the tool 200. As the tool 200 and anchor 10 are rotated, the anchor 10 member threads its way into the cortex 702 and underlining cancellous bone 704 to form a bone bore hole 720. The surgeon continues to rotate the tool 200 until the driving end 30 of the anchor 10 disengages from the socket of the engagement member 220 at which time the top 36 of the driving end 30 should be flush with, or below, the surface 701 of the bone 700, and all of the thread flights 60 are engaged in bone. At this time, the anchor 10 is emplaced in the bone and the surgeon may proceed to utilize the sutures 150 and 160 to affix soft tissue to the bone surface 701.

Figure 13:
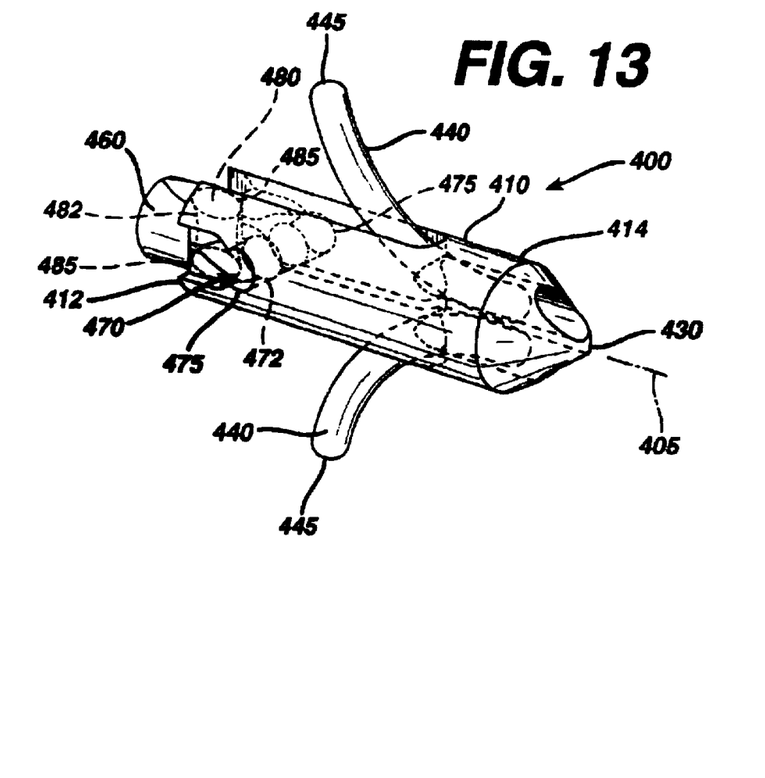
FIG. 13 illustrates an alternate embodiment of the present invention using an arced anchor.

Another embodiment of the suture anchors of the present invention is illustrated in FIG. 13. Seen is FIG. 13 is an arced anchor 400 having anchor member 410. Anchor member 410 is seen to be an elongated substantially cylindrical member having distal end 414 and proximal end 412. Anchor 400 is seen to have longitudinal axis 405. Extending distally from the distal end 414 is the conically shaped nose 430. Extending proximally from the proximal end 412 is the suture mounting stem 460. Seen to extend outwardly from the member 410 adjacent to the proximal end 412 are the arced members 440 having outward ends 414. Contained in the stem 460 is first suture mounting hole 470 having passage 472, and opposed openings 475 on either end of passage 472. Passage 470 is seen to be substantially perpendicular to axis 405. Second suture mounting hole 480 is seen to be located in stem 460, proximal to hole 470. Hole 480 is seen to have passage 482 and opposed openings 485 on either side of passage 482. It is preferred that the passages 470 and 480 be substantially perpendicular to each other, but may be otherwise angulated with respect to each other.

Figure 14:
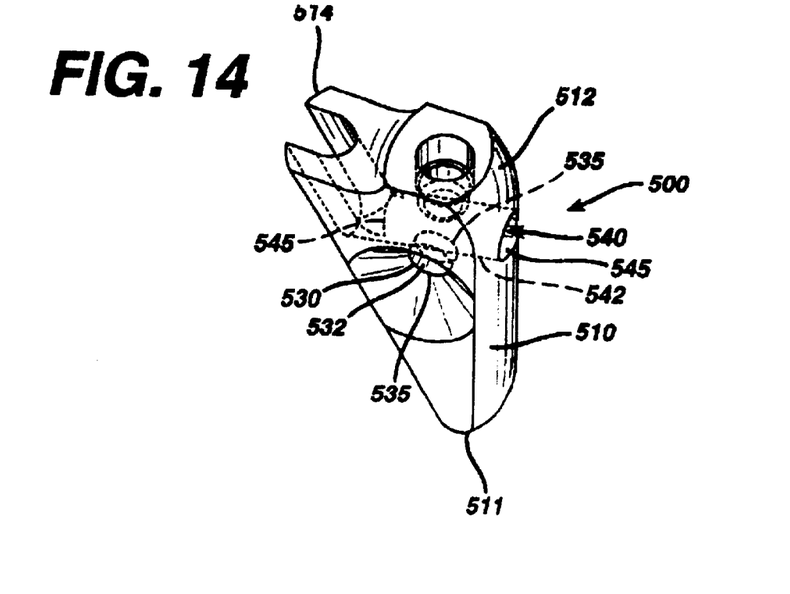
FIG. 14 illustrates yet another embodiment of the present invention using a wedge-type anchor

Yet another embodiment of a suture anchor of the present invention is wedge anchor 500 seen in FIG. 14. Anchor 500 is seen to have triangularly-shaped anchor body 510 having corners 511, 512 and 514. Anchor 500 is also seen to have first suture mounting hole 530 having passage 532 and opening 535 on either end of passage 532. Anchor 500 is also seen to have second suture mounting hole 540 which is substantially perpendicular to first mounting hole 530. Mounting hole 540 is seen to have passage 542 having opening 545 on either end of passage 542.

Figure 15:
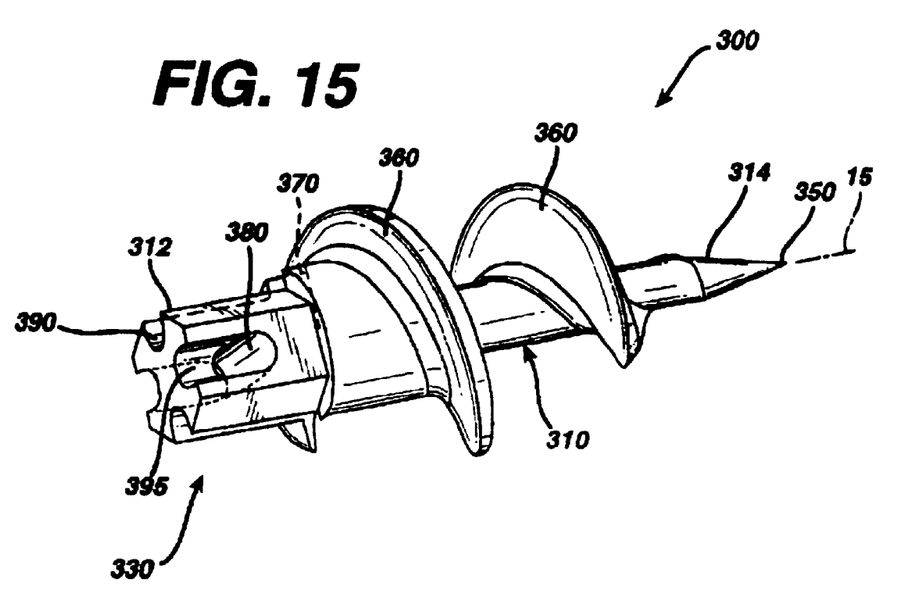
FIG. 15 illustrates another embodiment of a suture anchor of the present invention having a threaded body without a cutting flute.

FIG. 15 illustrates another embodiment of a suture anchor of the present invention. The suture anchor 300 is seen to be identical to the suture anchor 10 of FIG. 1, with the exception that it does not have a cutting flute. The anchor is seen to have anchor body 310, proximal end 312 and distal end 314. The anchor is also seen to have distal point 350, driving end 330, screw thread flights 360, first suture mounting hole 370, second suture mounting hole 380, first suture slots 390 and second suture slots 395.

The following example is illustrative of the principles and practice of the present invention.

EXAMPLE

A patient is prepared for surgery in a conventional manner using conventional anesthetic and surgical preparatory techniques. The patient is placed in a either a beach chair or lateral position. Full exposure of the coracoid process anteriorly and the entire scapula posteriorly is obtained. Decortication with a rasp, burr or drill bit is conducted prior to manual insertion. The minimum anchor spacing is 5 mm. Bone stock is determined to be adequate prior to placement. The anchor 10 of the present invention is screwed directly into the bone without predrilling. The inserter is twisted clockwise until the anchor is below the surface of the bone. If desired, the anchor is passed directly through soft tissue prior to insertion in the bone. The two sutures are then released from the inserter handle and the two sutures are used to fixate soft tissue to the bone. Specifically, the cuff tendon is secured to the humerus using the sutures, thereby completing the rotator cuff surgical repair. Multiple sutures are used with the anchor 10, and no tangling or binding is observed.

The suture anchors of the present invention are seen to have numerous advantages over the suture anchors of the prior art, which utilize multiple sutures. These advantages include the elimination of suture binding, tangling twisting, and inadvertent knotting. The use of the suture anchors of the present invention facilitates the attachment of soft tissue to bone in a surgical procedure and may improve the efficiency of the procedure.

Although this invention has been shown and described with respect to detailed embodiments thereof, it will be understood by those skilled in the art that various changes in form and detail may be made without departing from the spirit and scope of the claimed invention.

We claim:

1. A suture anchor comprising:
   a body member having a distal end, a proximal end, an outer surface and a longitudinal axis;
   a first suture passage extending through the body member, said first passage being substantially transverse to the longitudinal axis; and,
   a second suture passage extending through the body member, said second passage located proximal to the first suture passage, said second suture passage being substantially transverse to the longitudinal axis, wherein the second suture passage is angulated with respect to the first suture passage.

2. The suture anchor of claim 1 having a plurality of thread flights extending from the outer surface of the body member.

3. The suture anchor of claim 1 comprising a point extending from the distal end of the body member.

4. The suture anchor of claim 1 comprising a driving member extending proximally from the proximal end of the body member.

5. The suture anchor of claim 2 comprising a cutting flute in the body member.

6. The suture anchor of claim 1 comprising at least one arc member extending from the body member.

7. The suture anchor of claim 1, wherein the body member is compressible.

8. The suture anchor of claim 1 wherein the body member is cylindrically shaped.

9. The suture anchor of claim 1, wherein the body member is wedge shaped.

10. The anchor of claim 4, wherein the second suture passage is in the driving member.

11. The suture anchor of claim 1 wherein the second suture passage is angulated about 90 degrees with respect to the first suture passage.

12. The suture anchor of claim 1 having a plurality of suture grooves in the surface of the body member, such that a suture groove intersects each opening for the first and second suture passages.

13. A suture anchor comprising:
   a body member having a distal end, a proximal end, an outer surface and a longitudinal axis;
   a first suture passage extending through the body member, said first passage being substantially transverse to the longitudinal axis;
   a second suture passage extending through the body member, said second passage located proximal to the first suture passage, said second suture passage being substantially transverse to the longitudinal axis, wherein the second suture passage is angulated with respect to the first suture passage; and,
plurality of thread flights extending from the outer surface of the body member.

14. The anchor of claim 13 additionally comprising a distal point extending from the distal end of the body member.

15. The anchor of claim 13 additionally comprising a driving member extending proximally from the proximal end of the body member.

16. The suture anchor of claim 13 additionally comprising a cutting flute in the anchor body.

17. The anchor of claim 15, wherein the second suture passage is in the driving member.

18. The suture anchor of claim 13 wherein the second suture passage is angulated about 90 degrees with respect to the first suture passage.

19. The suture anchor of claim 13 having a plurality of suture grooves in the surface of the body member, such that a suture groove intersects each opening for the first and second suture passages.

20. The anchor of claim 15, wherein the driving member has a hexagonal cross-section.

* * * * *